United States Patent [19]

Perlin

[11] 4,210,131
[45] Jul. 1, 1980

[54] ARTIFICIAL SPHINCTER WITH COLLECTION BAG

[75] Inventor: Alfred R. Perlin, Highland Park, Ill.

[73] Assignee: The Kendall Company, Boston, Mass.

[21] Appl. No.: 928,043

[22] Filed: Jul. 26, 1978

[51] Int. Cl.² .............................................. A61B 19/00
[52] U.S. Cl. .................................. 128/1 R; 128/283; 128/DIG. 25
[58] Field of Search ............... 128/283, 1 R, 285, 128, 128/130, DIG. 25; 220/132 A, 230, 132 D

[56] References Cited

U.S. PATENT DOCUMENTS

| | | | |
|---|---|---|---|
| 1,491,011 | 4/1924 | Hodgin | 128/132 D |
| 1,810,466 | 6/1931 | Deutsch | 128/348 |
| 2,243,529 | 5/1941 | Grossman et al. | 128/283 |
| 2,324,520 | 7/1943 | Lamson | 128/283 |
| 2,455,859 | 12/1948 | Foley | 128/346 |
| 2,494,393 | 1/1950 | Lamson | 128/1 |
| 2,510,766 | 6/1950 | Surface | 128/1 |
| 2,533,924 | 12/1950 | Foley | 128/346 |
| 2,543,773 | 3/1951 | Goldschmidt | 32/2 |
| 2,564,399 | 8/1951 | Franken | 128/283 |
| 2,638,093 | 5/1953 | Kulick | 128/132 |
| 2,649,086 | 8/1953 | Sluijter | 128/1 R |
| 2,649,854 | 8/1953 | Salm | 128/1 |
| 2,696,209 | 12/1954 | Varaney | 128/132 R |
| 2,703,576 | 3/1955 | Furr, Jr. | 128/283 |
| 3,066,667 | 12/1962 | Berry | 128/1 |
| 3,080,865 | 3/1963 | Vincent | 128/98 |
| 3,083,704 | 4/1963 | Swearingen | 128/1 |
| 3,147,754 | 9/1964 | Koessler | 128/346 |
| 3,155,096 | 11/1964 | Outwin | 128/346 |
| 3,203,421 | 8/1965 | Bialick | 128/346 |
| 3,216,420 | 11/1965 | Smith et al. | 128/283 |
| 3,253,594 | 5/1966 | Matthews et al. | 128/348 |
| 3,372,695 | 3/1968 | Beliveau et al. | 128/1 |
| 3,384,073 | 5/1968 | Van Winkle | 128/1 |
| 3,419,008 | 12/1968 | Plishner | 128/346 |
| 3,503,400 | 3/1970 | Osthagen et al. | 128/349 |
| 3,538,917 | 11/1970 | Selker | 128/326 |
| 3,543,744 | 12/1970 | LePar | 128/283 |
| 3,554,184 | 1/1971 | Habib | 128/1 |
| 3,565,073 | 2/1971 | Giesy | 128/283 |
| 3,575,158 | 4/1971 | Summers | 128/1 |
| 3,613,661 | 10/1971 | Shah | 128/1 R |
| 3,642,004 | 2/1972 | Osthagen et al. | 128/349 R |
| 3,646,616 | 3/1972 | Keshin | 3/1 |
| 3,646,929 | 3/1972 | Bonnar | 128/1 R |
| 3,650,275 | 3/1972 | Von Der Mozel | 128/407 |
| 3,705,575 | 12/1972 | Edwards | 128/1 R |
| 3,705,580 | 12/1972 | Gauthier | 128/79 |
| 3,709,220 | 1/1973 | Boyden | 128/132 R |
| 3,730,186 | 5/1973 | Edmunds, Jr. et al. | 128/325 |
| 3,731,670 | 5/1973 | Loe | 128/1 R |
| 3,744,063 | 7/1973 | McWhorter et al. | 3/1 |
| 3,750,194 | 8/1973 | Summers | 3/1 |
| 3,758,073 | 9/1973 | Schulte | 251/342 |
| 3,768,102 | 10/1973 | Kwan-Gett et al. | 3/1 |
| 3,789,828 | 2/1974 | Schulte | 128/1 R |
| 3,797,478 | 3/1974 | Walsh | 128/1 R |
| 3,810,259 | 5/1974 | Summers | 3/1 |
| 3,812,841 | 5/1974 | Isaacson | 128/1 R |
| 3,815,576 | 6/1974 | Balaban | 128/1 R |
| 3,815,577 | 6/1974 | Bucalo | 128/1 R |
| 3,817,237 | 6/1974 | Bolduc | 128/1 R |
| 3,841,304 | 10/1974 | Jones | 128/1 R |
| 3,854,469 | 12/1974 | Giori et al. | 128/1 R |
| 3,863,622 | 2/1975 | Buuck | 128/1 R |
| 3,866,611 | 2/1975 | Baumrucker | 128/346 |
| 3,875,928 | 4/1975 | Angelchik | 128/1 R |
| 3,903,894 | 9/1975 | Rosen et al. | 128/346 |
| 3,924,631 | 12/1975 | Mancusl, Jr. | 128/346 |
| 3,926,175 | 12/1975 | Allen et al. | 128/1 R |
| 3,939,821 | 2/1976 | Roth | 128/1 R |
| 3,952,726 | 4/1976 | Hennig et al. | 128/1 R |
| 4,019,498 | 4/1977 | Hawtrey et al. | 128/1 R |
| 4,019,499 | 4/1977 | Fitzgerald | 128/1 R |
| 4,024,855 | 5/1977 | Bucalo | 128/1 R |
| 4,030,500 | 6/1977 | Ronnquist | 128/283 |
| 4,050,461 | 9/1977 | Ruby | 128/227 |
| 4,054,140 | 10/1977 | Etes | 128/283 |

FOREIGN PATENT DOCUMENTS 2717607  10/1978  Fed. Rep. of Germany .......... 128/1 R

*Primary Examiner*—John D. Yasko
*Attorney, Agent, or Firm*—Powell L. Sprunger

[57] ABSTRACT

An artificial sphincter for closure of a channel in a patient's body communicating with an opening adjacent the outside of the patient's body. The sphincter has a plug having a distal portion received in the channel, and a collection bag of flexible material covering the distal portion of the plug. The bag has a distal portion of reduced configurations received in the channel, with the bag inverting and the distal bag portion expanding to an enlarged configuration when the plug is removed from the channel in order to collect materials from the channel.

9 Claims, 8 Drawing Figures

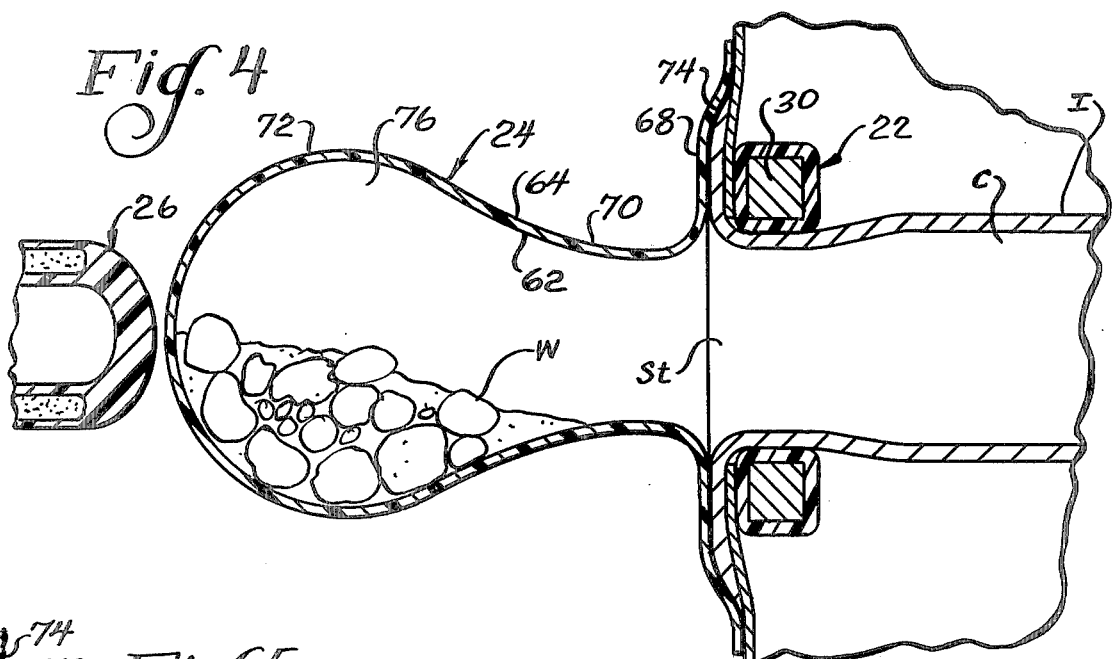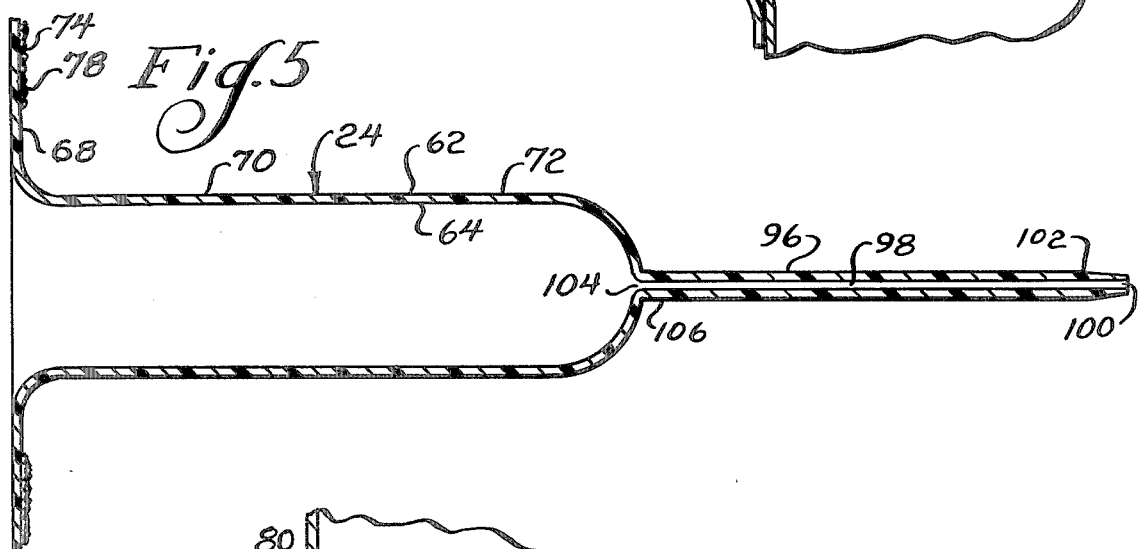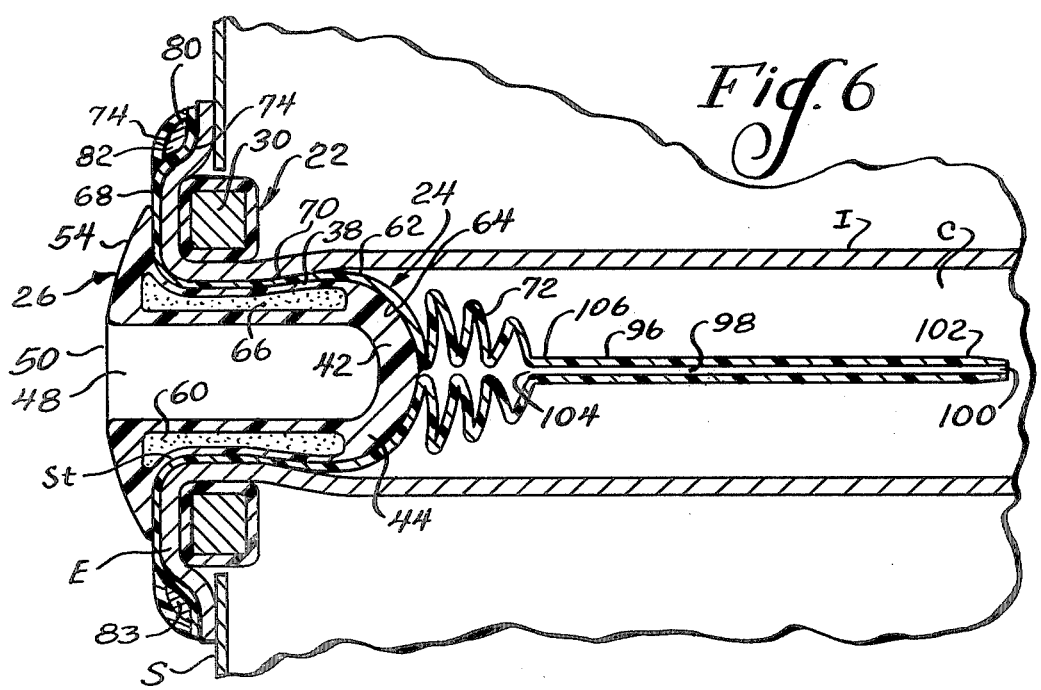

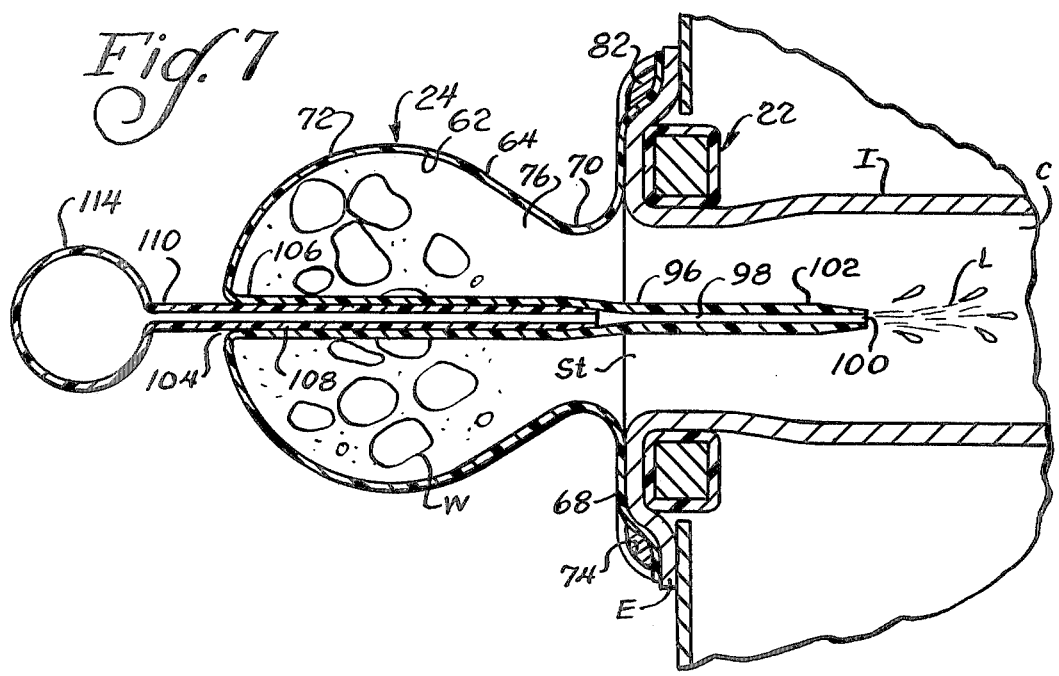
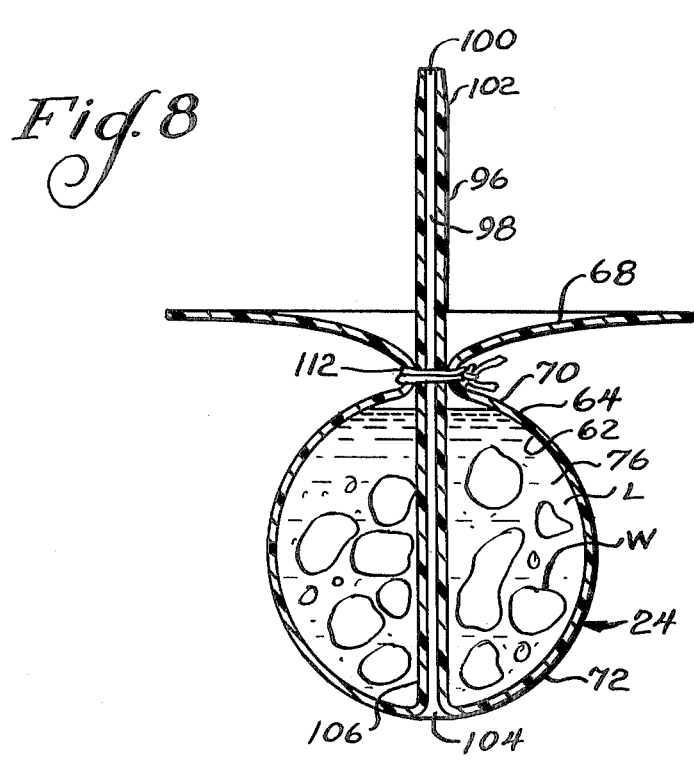

ARTIFICIAL SPHINCTER WITH COLLECTION BAG

BACKGROUND OF THE INVENTION

The present invention relates to closure devices, and more particularly to artificial sphincters.

A large number of temporary and permanent ostomy procedures are undertaken by surgeons each year to correct some difficulty in the intestinal tract, such as an obstruction or cancer in the tract. Most commonly, during the procedure the intestine is severed and an end of the intestine is brought through an incision in the abdominal wall. The surgeon then secures the intestine end adjacent the patient's skin, and forms an opening, termed a "stoma", at the juncture of the intestine and skin to permit passage of faecal matter outside the patient's body. In the case of a colostomy procedure, an end of the colon is joined to the skin to form the stoma. In the case of an ileostomy procedure, an end of the ileum is used to form the stoma, resulting in passage of corrosive fluids containing digestive enzymes and acids outside the patient's body.

The ostomy procedure results in loss of faecal continence for the patient, and, contrary to the patient's desire, many patients have been required to wear a bulky pouch on the outside of the body in order to collect the faecal matter passing through the stoma. In an attempt to overcome incontinence, many physicians have advised daily irrigation of the intestine by the patient through the stoma. However, the prior irrigation procedures have been very time consuming and inconvenient, and have not alleviated the need for use of stoma bags in many patients, particularly on social occasions. Surgical attempts have also been made to secure continence, such as by formation of a so-called "Kock Pouch", but the procedures have been accompanied by complications. It has also been proposed to achieve continence with various types of closure devices for the stoma.

SUMMARY OF THE INVENTION

A principal feature of the present invention is the provision of an improved artificial sphincter of simplified construction for closure of a channel in a patient's body communicating with an opening adjacent the outside of the patient's body.

The sphincter comprises, a generally annular member containing a first material for placement around the channel of the patient's body. The sphincter has a plug having an elongated outer wall of an elastic material for placement within the annular member in the body channel with the plug outer wall facing the walls of the channel in a closure position of the plug. The plug contains a particulate second material positioned in a region within the annular member when the plug is located in the closure position, with at least one of the first and second materials comprising a permanent magnetic material, and with the other of the first and second materials comprising a material substantially susceptible to the one magnetic material. The sphincter has a collection bag of flexible material having a first surface, a second opposed surface, a proximal portion extending peripherally around the body opening, and an elongated annular central portion for covering the outer plug wall in the closure position with the first surface of the central portion facing toward the body channel, and with the second surface of the central portion facing toward the plug outer wall. The bag has a distal portion extending distally from the central portion in the body channel, with the distal portion being folded into a configuration of reduced dimensions.

A feature of the present invention is that the bag protects the plug from corrosive fluids in the body channel while the plug is in said closure position.

Another feature of the invention is that a major part of the collection bag is located within the body channel during use of the sphincter to close the channel.

Thus, another feature of the invention is that the sphincter eliminates the need for a bulky receptacle located outside the patient's body for extended periods of time.

Still another feature of the invention is that when the plug is removed from the body channel, the bag automatically assumes an inverted configuration with the central and distal bag portions located outside the patient's body.

Yet another feature of the invention is that the distal portion of the inverted bag expands to a configuration of enlarged dimensions, such that the central and distal portions of the inverted bag define a cavity communicating with the body channel.

Another feature of the invention is that waste materials are permitted to pass from the body channel to the cavity in the inverted bag for collection therein.

A further feature of the invention is that the bag may be removed from the patient's body and may be discarded in a convenient and simplified manner.

Thus, a feature of the present invention is that the plug may be utilized to close the body channel for prolonged periods of time, and, after removal of the plug, the bag may be utilized to collect waste materials which have accumulated in the body channel during closure by the plug.

Still another feature of the invention is that the plug and bag may be placed in the body channel in a simplified manner.

The bag may also have a tubular section defining a narrow passageway extending from the distal portion of the bag.

A feature of the invention is that an irrigation liquid may be pumped through the passageway of the tubular section with the bag located in its inverted configuration in order to irrigate the body channel.

Yet another feature of the invention is that both the irrigation liquid and waste materials collect in the cavity defined by the inverted bag during the irrigation procedure.

A further feature of the invention is that the irrigation liquid may be discarded in the removed bag along with the collected waste materials after the irrigation procedure.

Thus, a feature of the invention is that the sphincter permits irrigation of the body channel in a simplified and convenient manner.

Further features will become more fully apparent in the following description of the embodiments of this invention and from the appended claims.

DESCRIPTION OF THE DRAWINGS

In the drawings:

FIG. 4 is a fragmentary sectional view illustrating use of the bag to collect waste materials passing from a channel in the patient's body;

FIG. 5 is a sectional view of another embodiment of a collection bag of the present invention;

FIG. 6 is a sectional view illustrating another embodiment of a collection bag of the present invention in a closure position of the bag and plug;

FIG. 7 is a sectional view illustrating use of the bag of FIG. 6 during an irrigation procedure; and FIG. 8 is a sectional view illustrating the bag of FIG. 7 as closed for disposal after the irrigation procedure has been completed.

DESCRIPTION OF THE PREFERRED EMBODIMENTS

Figure 1:
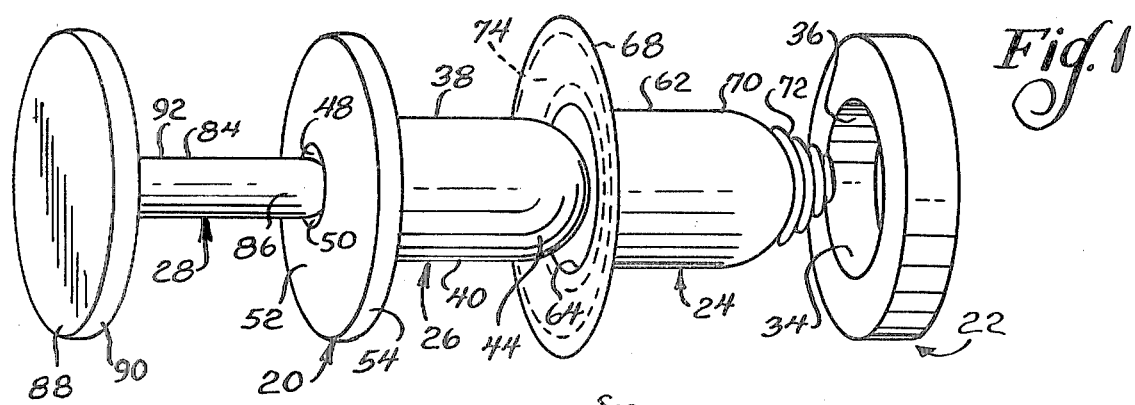
FIG. 1 is an exploded perspective view of an embodiment of an artificial sphincter of the present invention.
Figure 2:
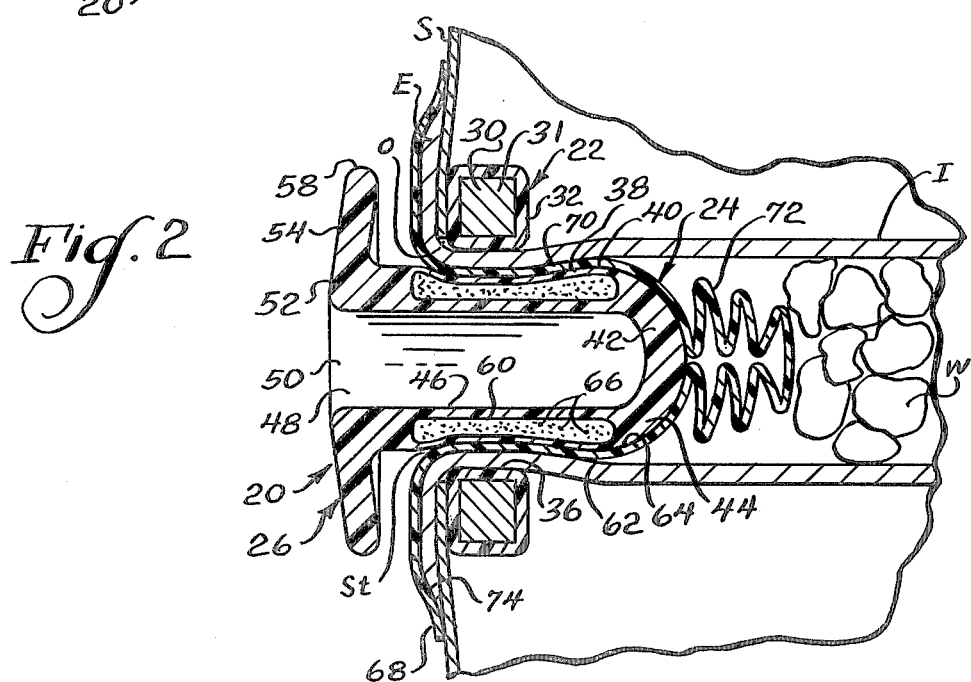
FIG. 2 is a sectional view of the sphincter of FIG. 1 illustrating a plug and a collection bag in a closure position in a patient's body.

Referring now to FIGS. 1 and 2, there is shown an artificial sphincter generally designated 20 having an annular member 22, a collection bag or receptacle 24, a plug 26, and an applicator 28. With reference to FIG. 2, the annular member 22 has a ring 30 of a first material 31, and an outer sheet 32 of a biologically inert material, such as silicone, covering the outer surface of the ring 30. As shown, an outer end E of an intestine I in a patient's body is brought through an opening or incision O adjacent the patient's skin S, with the intestine end E being secured to the patient's skin in order to form a stoma St, and with the annular member 22 extending around the intestine I within the patient's skin S, although the member 22 may be constructed to extend only partially around the intestine and for convenience will be termed annular. With reference to FIGS. 1 and 2, the annular member 22 has a relatively smooth inner surface 34 defining an opening 36 through which the intestine is passed, with the diameter of the opening 36 being approximately equal to the diameter of the intestine adjacent the skin S.

The plug 26 is constructed of an elastic material, such as a suitable plastic, and has an outer annular wall 38 defining an outer surface 40 facing toward the intestine I when the plug is placed in a closure position, and a distal wall 42 extending from the outer wall 38 and closing a distal end 44 of the plug. The plug 26 has an annular inner wall 46 defining an elongated central passageway 48 extending from the distal wall 42 to an opening 50 at a proximal end 52 of the plug 26, and an outwardly directed tubular rim 54 defining an outer edge 58 of the rim 54. As shown, the outer wall 38 and inner wall 46 at least partially define an elongated chamber 60 in the plug having a length greater than the length of the annular member 22. The plug also has a particulate second material 66 located in the chamber 60.

The bag 24 may be constructed of any suitable flexible material which is convenient for disposable use, such as a suitable plastic material. The bag has a first surface 62, an opposed second surface 64, an outwardly flared proximal portion or rim 68 extending peripherally around the bag, and an elongated annular central portion 70 extending distally from the proximal portion 68. The bag 24 also has a distal portion 72 extending distally from the central portion 70, with the distal portion 72 being folded or compacted into a configuration of reduced longitudinal dimensions, and with the distal portion 72 closing the distal end of the bag 24. As shown, a distal part of the plug 26 is received in the bag 24 while the bag and plug are in a closure position, such that the first surface 62 of the bag 24 faces toward the inner surface of the intestine I, and the second surface 64 of the bag 24 faces toward the outer surface 40 of the outer plug wall 38. The bag 24 may have suitable attachment means 74, such as a ring of adhesive, on the first surface 62 of the proximal portion 68 in order to releasably attach the proximal bag portion 68 to the intestine end E or the skin S of the patient peripherally around the stoma St.

The applicator 28 has an elongated rod 84 with a length greater than the length of the passageway 48 in the plug 26, such that a distal end 86 of the rod 84 is permitted to engage the distal wall 42 of the plug 26 when the applicator 28 is positioned in the passageway 48. The applicator 28 also has a handle 88 in the form of an outwardly directed rim 90 connected to a proximal end 92 of the rod 84.

At least one of said first and second materials 31 and 66 comprises a permanent magnetic material, such as a samarium-cobalt magnet, while the other of the first and second materials 31 and 66 comprises a material which is substantially susceptible to the one magnetic material, such as a magnetic material or a ferromagnetic material. With respect to magnetic properties, substances are generally classified as ferromagnetic, paramagnetic, and diamagnetic materials. A permeability $\mu$ is associated with substances, where $\mu = \mu_o$ for a vacuum ($\mu_o/4\pi = 10^{-7}$ Weber/amp-m.), $\mu$ is slightly greater than $\mu_o$ for paramagnetic materials, $\mu$ is slightly smaller than $\mu_o$ for diamagnetic materials, and $\mu$ is often much larger than $\mu_o$ for ferromagnetic materials. Apparently, iron, nickel and cobalt are technically considered the only ferromagnetic materials, but certain alloys display similar properties. Hence, for purposes under discussion, the term "ferromagnetic" will be taken in a broader sense to include materials which display properties akin to the classified ferromagnetic materials.

In a preferred form, the first material 31 in the ring 30 of the annular member 22 comprises a permanent magnetic material, which may be axially or radially magnetized, as desired. Although the second material 66 in the plug chamber 10 may comprise particles of a permanent magnetic material, in a preferred form, the second material 66 comprises a non-magnetized particulate ferromagnetic material, such as iron filings.

Figure 3:
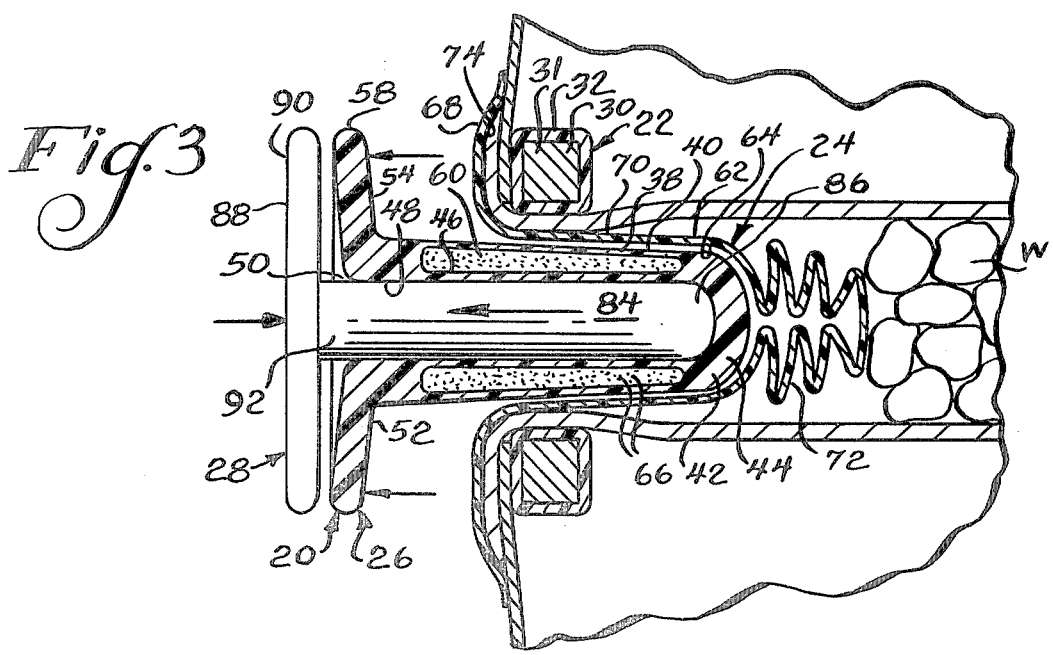
FIG. 3 is a sectional view of the sphincter of FIG. 1 illustrating use of an applicator to permit placement and removal of the plug.

In use, the bag 24 is placed in position over the plug 26, and the rod 84 of the applicator 28 is inserted into the passageway 48 of the plug 26. With reference to FIG. 3, the rim 54 of the plug 26 and the rim 90 of the applicator 28 are squeezed toward each other by the user, such that the distal end 86 of the rod 84 bears upon the distal end 44 of the plug 26 in order to stretch the plug 26 and outer wall 38 in a longitudinal direction. In this configuration, the transverse dimensions of the plug 26 in the region of the outer wall 38 are reduced to a size less than the diameter of the annular member 22 and a channel C in the intestine I, such that the plug 26 and bag 24 may be inserted through the stoma St into the channel C without significant contact against the walls of the intestine I. After placement of the plug in the intestine channel C, the applicator 28 may be released, and the susceptibility of the particulate second material 66 in the plug chamber 60 in combination with the elasticity of the plug walls causes the plug to assume a closure position with the outer plug wall 38 slightly engaging against the walls of the intestine I in the region around the annular member 22, as illustrated in FIG. 2. In this configuration, the plug 26 seals the stoma St and closes the channel C in the intestine I. The applicator 28 may be withdrawn from the passageway 48 to remove the applicator 28 from the plug 26 during use of the sphincter by the patient. When it is desired to remove the plug from the patient's body, the applicator 28 may be utilized to stretch the plug in a manner as previously described to withdraw the outer wall 38 of the plug 26 from the walls of the intestine I, and permit removal of the plug with minimal engagement against the walls of the intestine I.

With reference to FIG. 4, after the plug 26 has been removed from the intestine, due to pressure in the body channel C the bag 24 automatically assumes an inverted configuration with the central and distal portions 70 and 72 of the bag located outside the patient's body, and with the distal portion 72 of the bag expanding to a configuration of enlarged dimensions. In this configuration, the first surface 62 of the bag 24 defines a cavity 76 to receive waste material W which passes from the channel C of the intestine I into the bag cavity 76 for collection therein. After collection of the waste material in the bag 24, the bag may be removed from the patient's body and may be discarded. Another bag may be positioned over the plug for placement in the body channel C during subsequent closure of the intestine I.

Thus, in accordance with the present invention, the plug and bag are utilized to close the stoma St of the intestine during a prolonged period while waste materials are retained in the intestine by the plug. During this time, the bag 24 serves to protect the plug 26 from corrosive fluids and from soiling. When the plug is subsequently removed from the intestine, the bag automatically assumes an inverted and enlarged configuration due to pressure in the intestine channel C. The waste materials which have collected in the intestine pass through the stoma St into the bag cavity for convenient and simplified disposal.

Alternative embodiments of the present invention are illustrated in FIGS. 5 and 6, in which like reference numerals designate like parts. In this embodiment, the bag 24 has a proximal portion 68, a central portion 70, and a distal portion 72 which is folded into a configuration of reduced dimensions in a manner as previously described. In the embodiment of FIG. 5, the attachment means 74 comprises a ring of adhesive 78 on the first surface 62 of the proximal portion 68. In the embodiment of FIG. 6, the proximal portion 68 of the bag 24 defines an annular cavity 80 extending peripherally around the proximal portion 68. In this embodiment, the attachment means 74 comprises a ring 82 of a third material 83 which may be a solid or particulate permanent magnetic or ferromagnetic material. Thus, when the proximal portion 68 of the bag 24 is placed adjacent the intestine end E or skin S, the ring 82 is attracted toward the magnetic ring 30 of the annular member 22 in order to releasably attach the proximal bag portion 68 to the patient's body peripherally around the stoma St.

In the embodiments of FIGS. 5 and 6, the bag 24 has an elongated tubular section 96 extending distally from the distal bag portion 72. The tubular section 96 defines an elongated narrow passageway 98 extending through the tubular section 96, an aperture 100 at a distal end 102 of the tubular section 96, and an aperture 104 adjacent a proximal end 106 of the tubular section 96 at the juncture of the tubular section 96 and the distal bag portion 72. As shown, the tubular section 96 is located in the intestine channel C when the bag and plug are in the closure position.

With reference to FIG. 7, when the plug is removed from the intestine, the bag 24 automatically assumes an inverted and enlarged configuration such that the bag defines a cavity 76 to receive the waste material W in a manner as previously described. In this configuration, the tubular section 96 projects through the cavity 76 of the bag 24 into the intestine I. The elongated distal end 108 of a suitable pumping instrument 110 containing an irrigation liquid L may be inserted into the passageway 98 of the tubular section 96, as shown. Next, the irrigation liquid may be pumped by the instrument 110 through the passageway 98 and aperture 100 of the tubular section 96 into the intestine channel C, such as by squeezing a proximal bulb 114 of the instrument 110, in order to irrigate the intestine. As shown, the distal end 108 of the instrument 110 is spaced from the intestine wall to prevent inadvertent perforation of the intestine during the irrigation procedure. The pumped irrigation liquid L then passes from the intestine I into the cavity 76 of the inverted bag 24 for collection with the waste material W in the bag. With reference to FIG. 7, after the irrigation procedure has been completed, the central portion 70 of the bag 24 may be gathered and secured together at a location adjacent the proximal bag portion 68 by suitable means 112, such as a tie string, in order to close the bag cavity 76 for convenient disposal of the collected waste material W and the irrigation liquid L.

The foregoing detailed description is given for clearness of understanding only, and no unnecessary limitations should be understood therefrom, as modifications will be obvious to those skilled in the art.

I claim:

1. An artificial sphincter for closure of a channel in a patient's body communicating with an opening adjacent the outside of the patient's body, comprising:

a generally annular member containing a first material for placement at least partially around the channel of the patient's body;

a plug having an elongated outer wall of an elastic material for placement within said annular member in the body channel with the plug outer wall facing the walls of said channel in a closure position of the plug, said plug containing a particulate second material positioned in a region within the annular member when said plug is located in said closure position, with at least one of said first and second materials comprising a permanent magnetic material, and with the other of said first and second materials comprising a material substantially susceptible to said one magnetic material; and a collection bag of flexible material having a first surface, a second opposed surface, a proximal portion extending peripherally around said opening, means for releasably attaching the first surface of proximal portion to the patient's body peripherally around said opening, an elongated annular central portion for covering said outer plug wall in said closure position with the first surface of the central portion facing outwardly toward said body channel, and with the second surface of the central portion facing toward the plug outer wall, and said bag having a distal portion extending distally from said central portion in the body channel, with said distal bag portion being folded into a configuration of reduced dimensions, said bag being capable of assuming an inverted configuration when the plug is removed from the body channel with the central and distal bag portions located outside the patient's body, with said distal bag portion being expanded to a configuration of enlarged dimensions, and with the first surface of the inverted bag defining a cavity to receive materials passing from the body channel.

2. The sphincter of claim 1 wherein the attaching means comprises adhesive means on said proximal bag portion.

3. The sphincter of claim 1 wherein the attaching means comprises a third material extending around said proximal bag portion, with at least one of said first and third materials comprising a permanent magnetic material, and with the other of said first and third materials being substantially susceptible to the one magnetic material.

4. The sphincter of claim 1 wherein said distal portion comprises an elongated tubular sleeve being compressed to reduced longitudinal dimensions.

5. The sphincter of claim 1 wherein said bag includes an elongated narrow tubular section extending distally from said distal bag portion, said tubular section being of substantially smaller transverse dimension than that of said bag to fit within said bag when inverted within said bag and defining a narrow passageway and having a distal aperture, said tubular section being positioned in said cavity with the bag in said inverted configuration to permit irrigation of the body channel through said passageway.

6. An artificial sphincter for closure of a channel in a patient's body communicating with an opening adjacent the outside of the patient's body, comprising:

a generally annular member containing a first material for placement at least partially around the channel of the patient's body;

a plug having an elongated outer wall of an elastic material for placement within said annular member in the body channel with the plug outer wall facing the walls of said channel in a closure position of the plug, said plug containing a particulate second material positioned in a region within the annular member when said plug is located in said closure position, with at least one of said first and second materials comprising a permanent magnetic material, and with the other of said first and second materials comprising a material substantially susceptible to said one magnetic material; and a collection bag of flexible material having a first surface, a second opposed surface, a proximal portion extending peripherally around said opening, means for releasably attaching the first surface of said proximal portion to the patient's body peripherally around said opening, with said means including adhesive means, an elongated annular central portion for covering said outer plug wall in said closure position with the first surface of the central portion facing outwardly toward said body channel, and with the second surface of the central portion facing toward the plug outer wall, and said bag having a distal portion extending distally from said central portion in the body channel; with said distal bag portion being compressed into a configuration of reduced dimensions, said bag being capable of assuming an inverted configuration when the plug is removed from the body channel with the central and distal bag portions located outside the patient's body, with said distal bag portion being expanded to a configuration of enlarged dimensions, and with the first surface of the inverted bag defining a cavity to receive materials passing from the body channel.

7. An artificial sphincter for closure of a channel in a patient's body communicating with an opening adjacent the outside of the patient's body, comprising:

a generally annular member containing a first material for placement at least partially around the channel of the patient's body;

a plug having an elongated outer wall of an elastic material for placement within said annular member in the body channel with the plug outer wall facing the walls of said channel in a closure position of the plug, said plug containing a particulate second material positioned in a region within the annular member when said plug is located in said closure position, with at least one of said first and second materials comprising a permanent magnetic material, and with the other of said first and second materials comprising a material substantially susceptible to said one magnetic material; and a collection bag of flexible material having a first surface, a second opposed surface, a proximal portion extending peripherally around said opening, means for releasably attaching the first surface of said proximal portion to the patient's body peripherally around said opening, with said means including a third material extending around said proximal bag portion, with at least one of said first and third materials comprising a permanent magnetic material, and with the other of said first and third materials being substantially susceptible to the one magnetic material, an elongated annular central portion for covering said outer plug wall in said closure position with the first surface of the central portion facing outwardly toward said body channel, and with the second surface of the central portion facing toward the plug outer wall, and said bag having a distal portion extending distally from said central portion in the body channel, with said distal bag portion being compressed into a configuration of reduced dimensions, said bag being capable of assuming an inverted configuration when the plug is removed from the body channel with the central and distal bag portions located outside the patient's body, with said distal bag portions located outside the patient's body, with said distal bag portions being expanded to a configuration of enlarged dimensions, and with the first surface of the inverted bag defining a cavity to receive materials passing from the body channel.

8. An artificial sphincter for closure of a channel in a patient's body communicating with an opening adjacent the outside of the patient's body, comprising:

a generally annular member containing a first material for placement at least partially around the channel of the patient's body;

a plug having an elongated outer wall of an elastic material for placement within said annular member in the body channel with the plug outer wall facing the walls of said channel in a closure position of the plug, said plug containing a particulate second material positioned in a region within the annular member when said plug is located in said closure position, with at least one of said first and second materials comprising a permanent magnetic material, and with the other of said first and second materials comprising a material substantially susceptible to said one magnetic material; and a collection bag of flexible material having a first surface, a second opposed surface, a proximal portion extending peripherally around said opening, means for releasably attaching the first surface of said proximal portion to the patient's body peripherally around said opening, with said means including adhesive means, an elongated annular central portion for covering said outer plug wall in said closure position with the first surface of the central portion facing outwardly toward said body channel, and with the second surface of the central portion facing toward the plug outer wall, and said bag having a distal portion extending distally from said central portion in the body channel, with said distal bag portion being compressed into a configuration of reduced dimensions, said bag being capable of assuming an inverted configuration when the plug is removed from the body channel with the central and distal bag portions located outside the patient's body, with said distal bag portion being expanded to a configuration of enlarged dimensions, and with the first surface of the inverted bag defining a cavity to receive materials passing from the body channel, said distal bag portion including an elongated tubular section extending distally from said distal bag portion, said tubular section being of substantially smaller transverse dimension than that of said bag to fit within said bag when inverted within said bag and defining a narrow passageway and having a distal aperture, said tubular section being positioned in said cavity with the bag in said inverted configuration to permit irrigation of the body channel through said passageway.

9. An artificial sphincter for closure of a channel in a patient's body communicating with an opening adjacent the outside of the patient's body, comprising:

a generally annular member containing a first material for placement at least partially around the channel of the patient's body;

a plug having an elongated outer wall of an elastic material for placement within said annular member in the body channel with the plug outer wall facing the walls of said channel in a closure position of the plug, said plug containing a particulate second material positioned in a region within the annular member when said plug is located in said closure position, with at least one of said first and second materials comprising a permanent magnetic material, and with the other of said first and second materials comprising a material substantially susceptible to said one magnetic material; and a collection bag of flexible material having a first surface, a second opposed surface, a proximal portion extending peripherally around said opening, means for releasably attaching the first surface of said proximal portion to the patient's body peripherally around said opening, with said means including a third material extending around said proximal bag portion, with at least one of said first and third materials comprising a permanent magnetic material, and with the other of said first and third materials being substantially susceptible to the one magnetic material, an elongated annular central portion with the first surface of the central portion facing outwardly toward said body channel, and with the second surface of the central portion facing toward the plug outer wall, and said bag having a distal portion extending distally from said central portion in the body channel, with said distal bag portion being compressed into a configuration of reduced dimensions, said bag being capable of assuming an inverted configuration when the plug is removed from the body channel with the central and distal bag portions located outside the patient's body, with said distal bag portion being expanded to a configuration of enlarged dimensions, and with the first surface of the inverted bag defining a cavity to receive materials passing from the body channel;

said distal bag portion including an elongated tubular section extending distally from said distal bag portion, said tubular section being of substantially smaller transverse dimension than that of said bag to fit within said bag when inverted within said bag and defining a narrow passageway and having a distal aperture, said tubular section being positioned in said cavity with the bag in said inverted configuration to permit irrigation of the body channel through said passageway.

* * * * *